(12) United States Patent
Kantor

(10) Patent No.: US 10,086,177 B2
(45) Date of Patent: Oct. 2, 2018

(54) BALLOON CATHETER WITH ELASTOMERIC SHEATH AND METHODS

(71) Applicant: Medtronic Vascular, Inc., Santa Rosa, CA (US)

(72) Inventor: John Kantor, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 264 days.

(21) Appl. No.: 15/061,121

(22) Filed: Mar. 4, 2016

(65) Prior Publication Data
US 2016/0184560 A1    Jun. 30, 2016

Related U.S. Application Data

(62) Division of application No. 14/151,107, filed on Jan. 9, 2014.

(51) Int. Cl.
| | | |
|---|---|---|
| *A61M 25/10* | (2013.01) | |
| *B32B 37/14* | (2006.01) | |
| *B32B 38/10* | (2006.01) | |
| *B32B 43/00* | (2006.01) | |
| *B05D 1/28* | (2006.01) | |

(52) U.S. Cl.
CPC ........ *A61M 25/1002* (2013.01); *A61M 25/10* (2013.01); *A61M 25/1038* (2013.01); *B05D 1/286* (2013.01); *B32B 37/142* (2013.01); *B32B 38/10* (2013.01); *B32B 43/006* (2013.01); *A61M 2025/1004* (2013.01); *A61M 2025/105* (2013.01); *A61M 2025/1031* (2013.01); *A61M 2025/1068* (2013.01); *A61M 2025/1081* (2013.01); *B32B 2535/00* (2013.01)

(58) Field of Classification Search
CPC .. A61M 2025/1004; A61M 2025/1031; A61M 2025/105; A61M 2025/1068; A61M 2025/1081; A61M 25/10; A61M 25/1002; A61M 25/1038; B05D 1/286; B05D 2535/00; B05D 37/142; B05D 38/10; B05D 43/006

See application file for complete search history.

(56) References Cited

U.S. PATENT DOCUMENTS

| | | |
|---|---|---|
| 5,876,374 A | 3/1999 | Alba |
| 7,704,545 B2 | 4/2010 | Kantor |
| 7,750,041 B2 | 7/2010 | Speck et al. |
| 8,257,305 B2 | 9/2012 | Speck et al. |
| 2010/0228333 A1 | 9/2010 | Drasler et al. |
| 2011/0054396 A1 | 3/2011 | Kangas et al. |
| 2012/0283636 A1 | 11/2012 | Rizq et al. |

FOREIGN PATENT DOCUMENTS

| | | |
|---|---|---|
| WO | WO2009/018816 A2 | 2/2009 |
| WO | WO2009/018816 A3 | 1/2010 |
| WO | WO2013015025 | 1/2013 |
| WO | WO2013/044942 | 4/2013 |

*Primary Examiner* — Imani Hayman

(57) ABSTRACT

Balloon catheters that include a balloon and an elastomeric sheath, each having a surface with a therapeutic agent disposed thereon, along with methods of making and methods of using the disclosed balloon catheters.

9 Claims, 4 Drawing Sheets

BALLOON CATHETER WITH ELASTOMERIC SHEATH AND METHODS

RELATED APPLICATION

This application is a Division of and claims the benefit of U.S. patent application Ser. No. 14/151,107, filed Jan. 9, 2014, the disclosure of which is incorporated by reference in its entirety.

BACKGROUND

Using targeted delivery, a controlled dose of a therapeutic agent may be delivered directly to a target site, e.g., a lesion in a diseased vessel, while avoiding or minimizing exposing other parts of the body to the agent. Also, greater amounts of therapeutic agent may be delivered to the afflicted parts of the body. In one approach to localized delivery, a balloon catheter is used, wherein the balloon has therapeutic agent disposed on its outer surface and is expanded within a vessel to deliver the therapeutic agent to the vessel wall. In an alternative approach, an expandable sheath is disposed around a balloon and a coating disposed on the expandable sheath, the coating including a therapeutic agent. There is still a need for improved balloon catheter devices for delivery of one or more therapeutic agents to an intravascular site.

SUMMARY

The present disclosure provides balloon catheters that include a balloon and an elastomeric sheath, each having a surface with a therapeutic agent disposed thereon. The present disclosure also provides methods of making and methods of using the disclosed balloon catheters.

In one embodiment of the present disclosure, there is provided a balloon catheter that includes: an elongated catheter shaft having proximal and distal ends, wherein the catheter shaft defines a longitudinal axis extending between the proximal and distal ends; an inflatable balloon (preferably, in a folded inflatable state) located close to the distal end of the catheter shaft, wherein the balloon includes a polymeric material having a surface with a first therapeutic agent disposed thereon; and an elastomeric sheath including an elastomeric material having a surface with a second therapeutic agent disposed thereon; wherein in a first configuration the inflatable balloon is located within the elastomeric sheath such that expansion of the inflatable balloon to an inflated state expands the elastomeric sheath, and wherein in a second configuration the inflatable balloon is located outside of the elastomeric sheath, and further wherein the balloon and the elastomeric sheath are configured for movement relative to each other along the longitudinal axis between the first configuration and the second configuration when deployed within a body lumen.

In certain embodiments, the balloon catheter further includes a protective sheath positioned around the elastomeric sheath, wherein the protective sheath is configured for movement relative to the elastomeric sheath along the longitudinal axis, when deployed in a body lumen, between a first configuration in which the elastomeric sheath is positioned within the protective sheath and a second configuration in which at least a portion of the elastomeric sheath is located outside of the protective sheath.

The present disclosure provides methods of making and methods of using the disclosed catheter balloons.

In one embodiment, there is provided a method of manufacturing a balloon catheter as described herein. The method includes: providing an elongated catheter shaft having proximal and distal ends with an inflatable balloon located close to the distal end of the catheter shaft, wherein the balloon includes a polymeric material having a surface; positioning a delivery sheath around the balloon, wherein the delivery sheath includes a polymeric material having a therapeutic agent impregnated therein or coated thereon; and applying conditions effective to transfer (e.g., diffuse) the therapeutic agent from the delivery sheath to the surface of the inflatable balloon.

In another embodiment of manufacturing a balloon catheter as described herein, the method further includes: removing the delivery sheath from the balloon; positioning an elastomeric sheath around the balloon, wherein the elastomeric sheath includes an elastomeric material having a surface; positioning a delivery sheath around the elastomeric sheath, wherein the delivery sheath includes a polymeric material having a therapeutic agent impregnated therein or coated thereon; and applying conditions effective to transfer (e.g., diffuse) the therapeutic agent from the delivery sheath to the surface of the elastomeric sheath.

In certain embodiments, the balloon and the elastomeric sheath are provided with the therapeutic agent separately provided (i.e., the elastomeric sheath is previously prepared and provided with the therapeutic agent, and successively it is combined with a balloon previously coated with a therapeutic agent).

In one embodiment of the present disclosure, there is provided a method of delivering one or more therapeutic agents to a diseased vessel. The method includes: providing a balloon catheter as described herein; advancing the balloon catheter into the diseased vessel; inflating the inflatable balloon to form an inflated balloon and an expanded sheath that contacts the wall of the diseased vessel and thereby delivers the second therapeutic agent from the surface of the expanded sheath to a first site of the diseased vessel; deflating the inflated balloon to reform the inflatable balloon into a reformed inflatable balloon; removing the elastomeric sheath from around the reformed inflatable balloon; and inflating the reformed inflatable balloon to contact the wall of the diseased vessel with the first therapeutic agent to deliver the first therapeutic agent from the surface of the inflated balloon to the first site, or to a different site of the same or a different diseased vessel if the reformed inflatable balloon is moved to the different site after the expanded sheath contacts the wall of the diseased vessel and before inflating the reformed inflatable balloon.

In another embodiment of the present disclosure, there is provided a method of delivering one or more therapeutic agents to a diseased vessel. The method includes: providing a balloon catheter that includes: an elongated catheter shaft having proximal and distal ends; a folded inflatable balloon located close to the distal end of the catheter shaft, wherein the balloon includes a polymeric material having a surface with a first therapeutic agent disposed thereon; and an elastomeric sheath positioned around the inflatable balloon such that the inflatable balloon is located within the elastomeric sheath, wherein the sheath includes an elastomeric material having a surface with a second therapeutic agent disposed thereon. The method further includes: advancing the balloon catheter into the diseased vessel (i.e., one having a vascular lesion); inflating the folded inflatable balloon to form an inflated balloon and an expanded sheath that contacts the wall of the diseased vessel and thereby delivers the second therapeutic agent from the surface of the expanded sheath to a first site of the diseased vessel; deflating the inflated balloon after delivering the second therapeutic agent to the first site to reform the inflatable balloon into a reformed inflatable balloon (herein, a "reformed" inflatable balloon may or may not be refolded, and may or may not be the same degree of "deflation" of the initial inflatable balloon); removing the elastomeric sheath from around the reformed inflatable balloon; and inflating the reformed inflatable balloon to contact the wall of the diseased vessel with the first therapeutic agent to deliver the first therapeutic agent from the surface of the inflated reformed inflatable balloon to the first site, or to a different site of the same or a different diseased vessel if the reformed inflatable balloon is moved to the different site after the expanded sheath contacts the wall of the diseased vessel and before inflating the reformed inflatable balloon.

In yet another embodiment of the present disclosure, there is provided a method of delivering one or more therapeutic agents to a diseased vessel. The method includes: providing a balloon catheter that includes: an elongated catheter shaft having proximal and distal ends; an inflatable balloon (preferably, a folded inflatable balloon) located close to the distal end of the catheter shaft, wherein the balloon has a proximal end and a distal end, and wherein the balloon includes a polymeric material having a surface with a first therapeutic agent disposed thereon; an elastomeric sheath positioned around the inflatable balloon such that the inflatable balloon is located within the elastomeric sheath, wherein the sheath includes an elastomeric material having a surface with a second therapeutic agent disposed thereon, and wherein the elastomeric sheath is longer than the inflatable balloon; and a protective sheath positioned around the elastomeric sheath and the inflatable balloon. The method further includes: advancing the balloon catheter into the diseased vessel; retracting the protective sheath towards the proximal end of the catheter shaft so that the inflatable balloon is not located in the protective sheath; inflating the inflatable balloon to form an inflated balloon and an expanded sheath that contacts the wall of the diseased vessel and thereby delivers the second therapeutic agent from the surface of the expanded sheath to a first site of the diseased vessel; deflating the inflated balloon to reform the inflatable balloon into a reformed inflatable balloon (herein, this "first reformed" inflatable balloon may or may not be refolded, and may or may not be the same degree of "deflation" of the initial inflatable balloon); retracting the protective sheath proximally towards the proximal end of the catheter shaft so that the reformed inflatable balloon is not located in the protective sheath after delivering the second therapeutic agent to the first site; retracting the reformed inflatable balloon proximally towards the proximal end of the catheter shaft within the elastomeric sheath (after delivering the second therapeutic agent to the first site); inflating the reformed inflatable balloon (after retracting the reformed inflatable balloon and the protective sheath proximally) so that the elastomeric sheath contacts the wall of the diseased vessel and thereby delivers the second therapeutic agent to a second site that is located proximally from the first site of the diseased vessel; and deflating the reformed inflated balloon to again reform a reformed inflatable balloon after delivering the second therapeutic agent to the second site (herein, a "second reformed" inflatable balloon may or may not be refolded, and may or may not be the same degree of "deflation" of the initial inflatable balloon or the "first reformed" inflatable balloon); retracting the elastomeric sheath proximally towards the proximal end of the catheter shaft so that the reformed inflatable balloon is not located in the protective sheath or the elastomeric sheath after delivering the second therapeutic agent to the second site; and inflating the reformed inflatable balloon (after retracting the elastomeric sheath proximally) to form an inflated balloon that contacts the wall of the diseased vessel and thereby delivers the first therapeutic agent from the surface of the inflated balloon to the second site of the diseased vessel or to a third site of the diseased vessel if the inflated balloon is moved to a different site after delivering the second therapeutic agent to the second site.

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Herein, "located close to the distal end of the catheter shaft" means located closer to the distal end of the catheter shaft than the proximal end of the catheter shaft. Preferably, in certain embodiments "located close to the distal end of the catheter shaft" means located at the ultimate distal end of the catheter shaft.

The terms "polymer" and "polymeric material" (including elastomer and elastomeric polymer) include, but are not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DRAWINGS

The disclosure may be more completely understood in connection with the following drawings.

Figure 3A:
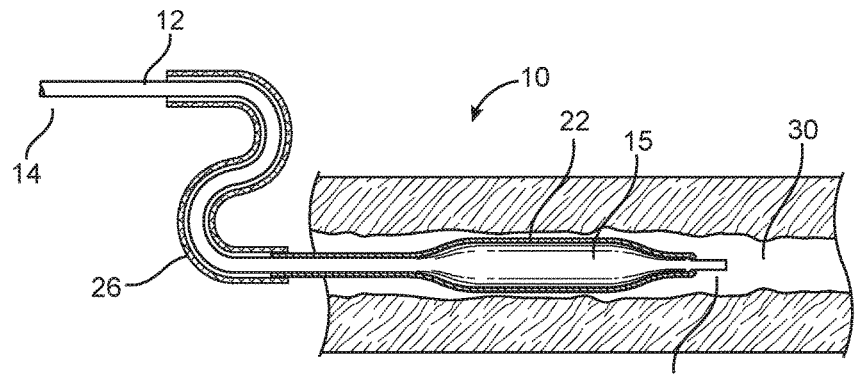
Figure 3B:
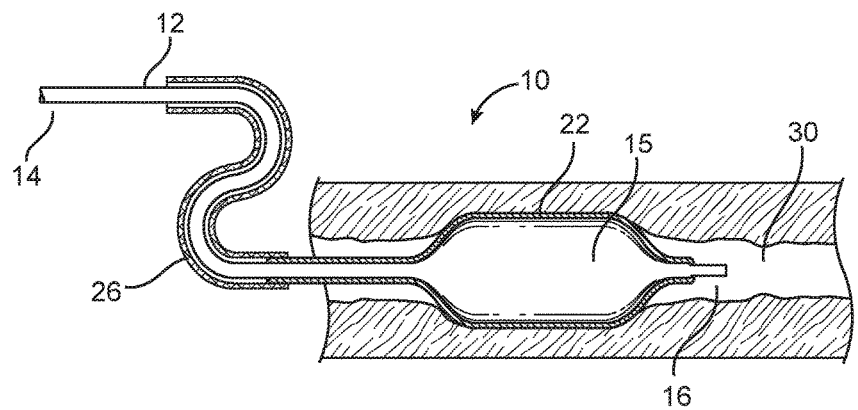
Figure 3C:
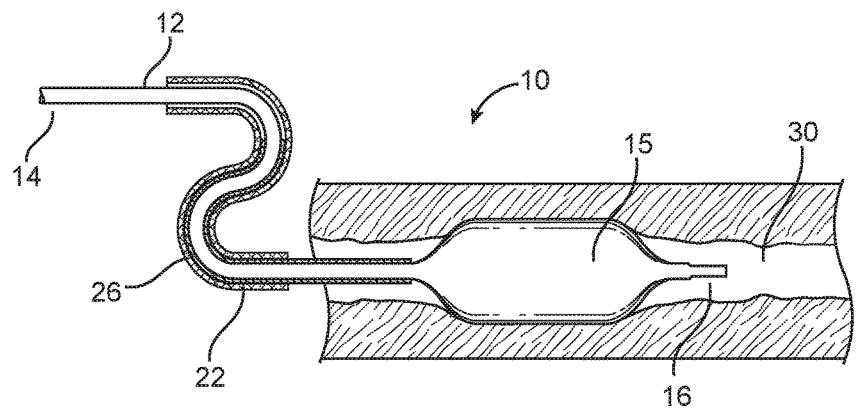

FIG. 3A-3C disclose the steps of a method of delivering a therapeutic agent to a diseased vessel according to an embodiment of the present disclosure, and FIG. 4A-4D disclose the steps of a method of delivering a therapeutic agent to a diseased vessel according to a further embodiment of the present disclosure.

DETAILED DESCRIPTION OF ILLUSTRATIVE EMBODIMENTS

The present disclosure relates to balloon catheters that include a balloon and an elastomeric sheath, each having a surface with a therapeutic agent disposed thereon.

Balloon Catheter

Figure 1:
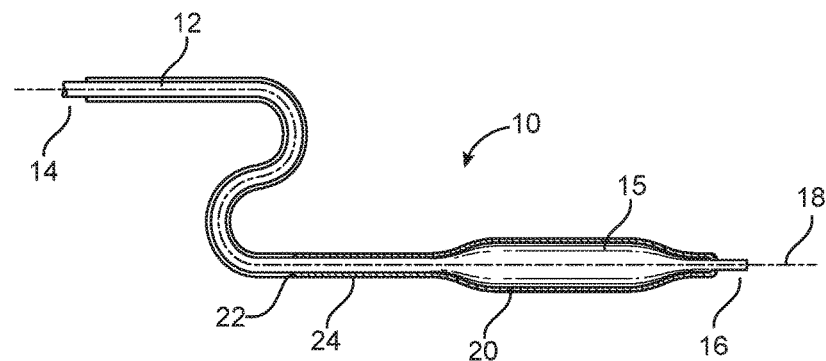
FIG. 1 is a partial longitudinal section of an exemplary embodiment of a balloon catheter with an elastomeric sheath.

Referring to FIG. 1, in one exemplary embodiment of the present disclosure, there is provided a balloon catheter 10 that includes: an elongated catheter shaft 12 having a proximal end 14 and a distal end 16, wherein the catheter shaft defines a longitudinal axis 18 extending between the proximal end 14 and distal end 16; a balloon 15 in an inflatable state (preferably, in a folded state) located close to the distal end 16 of the catheter shaft 12 (i.e., closer to the distal end 16 of the catheter shaft 12 than the proximal end 14 of the catheter shaft 12). The balloon 15 includes a polymeric material having a surface 20 with a first therapeutic agent disposed thereon (as a result of the therapeutic agent being coated on the surface or impregnated into the polymeric material). The balloon catheter also includes an elastomeric sheath 22 including an elastomeric material having a surface 24 with a second therapeutic agent disposed thereon (as a result of the therapeutic agent being coated on the surface or impregnated into the elastomeric material). It is noted that although the elastomeric sheath 22 runs along the whole length of the catheter to allow it to be retrieved proximally, the whole length of the elastomeric sheath does not necessarily have the second therapeutic agent disposed thereon (hatched region of sheath 22 indicates that portion of the sheath with therapeutic agent disposed thereon), but only the distal portion thereof, in correspondence of the balloon.

Figure 2:
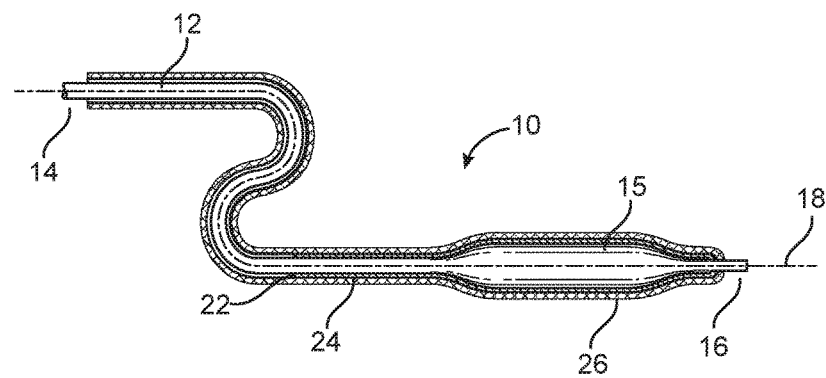
FIG. 2 is a partial longitudinal section of an exemplary embodiment of a balloon catheter with an elastomeric sheath and an optional protective sheath.

In certain embodiments of the present disclosure, as shown in FIG. 2, the balloon catheter 10 includes an optional protective sheath 26 positioned around the elastomeric sheath 22, which is positioned around the balloon 15.

As shown in FIG. 3, in a first configuration (FIG. 3A) the protective sheath 26 has been retracted proximally and the inflatable balloon 15 (as shown in a folded state) is located within the elastomeric sheath 22 such that expansion of the inflatable balloon 15 to an inflated state (preferably, a first inflated state) expands the elastomeric sheath 22 (as shown in FIG. 3B). In a second configuration (FIG. 3C) the elastomeric sheath 22 has been retracted proximally and the inflatable balloon 15 is located outside of the elastomeric sheath (preferably, for expansion to a second inflated state), the balloon 15 and the elastomeric sheath 22 being configured for movement relative to each other along the longitudinal axis 18 (see FIG. 1) between the first configuration (FIG. 3A) and the second configuration (FIG. 3C) when deployed within a body lumen.

In certain embodiments of the present disclosure, as shown in FIG. 2, the balloon catheter 10 includes a protective sheath 26 positioned around the elastomeric sheath 22. The protective sheath 26 is configured for movement relative to the elastomeric sheath 22 along the longitudinal axis 18, when deployed in a body lumen, between a first configuration (FIG. 2) in which the elastomeric sheath 22 is positioned within the protective sheath 26 and a second configuration (FIGS. 3A-3C) in which at least a portion of the elastomeric sheath 22 is located outside of the protective sheath 26.

The balloon 15 of the balloon catheter 10 may be any of a variety of conventional balloons for use in balloon catheters. They may be of any of a variety of lengths, diameters, thicknesses, etc., as is needed for the particular use. Typically, the length of the balloon is selected such that the diseased vessel includes a vascular lesion having a length that is longer than the balloon length. The balloon may be compliant, semi-compliant, or non-compliant. Semi-compliant and non-compliant balloons are most useful for peripheral indications. An exemplary material for the balloon is any of a wide variety of grades of nylon (e.g., nylon-12). The balloon may be made of a variety of other conventional polymeric materials, such as polyethylene terephthalate (PET), polyethylene (PE), high density polyethylene (HDPE), polyamide copolymers, polyurethanes, polyvinyl chloride, blends, copolymers, and multi-layered combinations thereof.

Typically, the elastomeric sheath 22 portion that is loaded with the therapeutic agent (hatched region of sheath 22) is longer than the balloon 15 (FIG. 1). In some embodiments, the elastomeric sheath 22 portion that is loaded with the therapeutic agent (hatched region of sheath 22) is positioned around the balloon 15 and at least a portion of the catheter shaft 12 close to the balloon proximal end. The wall thickness of the elastomeric sheath may be 0.001 inch, for example. The elastomeric sheath may be made of a variety of elastomeric materials. Herein, an elastomeric material is a polymeric material that resembles rubber because it generally resumes its original shape when a deforming force is removed. An exemplary material for the elastomeric sheath is polytetrafluoroethylene (PTFE). The elastomeric sheath may be made of a variety of other elastomeric materials, such as polyamides, polyurethanes, polyvinyl chloride, blends, copolymers, and multi-layered combinations thereof.

Typically, the optional protective sheath 26 is at least as long as the elastomeric sheath 22 (FIG. 2). The wall thickness of the protective sheath may be 0.001 inch, for example, or thicker. The protective sheath may be made of the same material as the elastomeric sheath, although this is not a requirement. The protective sheath may be made of a variety of other polymeric materials, such as polyethylene (PE) and high density polyethylene (HDPE). Blends, copolymers, and multi-layered combinations of such materials may be used in the protective sheath.

The therapeutic agent may be any of a variety of therapeutic agents. Typically, these include agents for treating heart disease, various cardiovascular ailments, and other vascular conditions, including blockages, occlusions, stenoses or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

Preferred therapeutic agents are those capable of producing a beneficial effect against one or more conditions including coronary restenosis, cardiovascular restenosis, angiographic restenosis, arteriosclerosis, hyperplasia, and other diseases or conditions. For example, the therapeutic agent may be selected to inhibit or prevent vascular restenosis, a condition corresponding to a narrowing or constriction of the diameter of the bodily lumen where a stent is placed. An antirestenotic drug such as rapamycin, a rapamycin analogue, or a rapamycin derivative may be used to prevent or reduce the recurrence or narrowing and blockage of the bodily vessel. Another preferred therapeutic agent is the antirestenotic drug paclitaxel.

Alternatively, the therapeutic agent may be an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a recombinant DNA product, a recombinant RNA product, an antisense compound, a collagen, a collagenic derivative, a protein, a protein analog, a saccharide, a saccharide derivative, a bioactive agent, other pharmaceutical drugs, or a combination thereof.

The first and second therapeutic agents may be the same or different therapeutic agents and/or they may be at different concentrations. Two different therapeutic agents may be used, e.g., to fight different events that lead to restenosis (e.g., smooth muscle cell migration and fibrin deposition).

The amount of the therapeutic agent applied to the balloon and elastomeric sheath may vary depending on the characteristics of the particular agent or combination of agents, the length of time the balloon or elastomeric sheath is in place and other factors. Generally, the dose of therapeutic agent disposed on a balloon or elastomeric sheath of the present disclosure ranges from nanograms to milligrams. In one embodiment, the therapeutic agent is coated to achieve a total amount disposed on the surface of the balloon or elastomeric sheath of at least 1 microgram per square millimeter (1 µg/mm$^2$). In another embodiment, the amount disposed on the surface of the balloon or elastomeric sheath is up to 1000 micrograms per square millimeter (µg/mm$^2$). Typically the therapeutic agent is coated to achieve a total amount disposed on the surface of the balloon or elastomeric sheath in a range from about 1 µg/mm$^2$ to about 5 µg/mm$^2$.

The therapeutic agent may be disposed on, and preferably adhered to, the balloon and elastomeric sheath with or without the use of any binding agents, e.g., polymeric binders. If binding agents are used, examples of such agents include, for example, urea, azides, gels, biodegradable/bioabsorbable polymers.

Methods of Making

The therapeutic agent may be applied to the balloon and elastomeric sheath using a variety of coating or impregnating techniques, for example. Balloons and elastomeric sheaths can be coated with a therapeutic agent (e.g., drug) coating solution by application techniques such as dipping, spraying, painting, and brushing (e.g., U.S. Pat. No. 8,257,305 and U.S. Pat. No. 7,750,041; and International Pub. No. WO 2009/018816). In many of the current balloon coating methods, a coating solution that includes at least one therapeutic agent and a solvent is applied to a balloon to form a substantially uniform layer of therapeutic agent. The concentration of the therapeutic agent applied to the balloon and elastomeric sheath of the present disclosure varies depending on the therapeutic agent intended use.

In one embodiment, there is provided a method of manufacturing a balloon catheter as described herein using a delivery sheath. Such method is analogous to the method described in U.S. Pat. No. 7,704,545 for applying a drug to a stent. In various embodiments, the delivery sheath is coated with a therapeutic agent (and a polymer). In certain embodiments, the delivery sheath can be impregnated with a therapeutic agent.

The delivery sheath may be made of a flexible material suitable for positioning around the balloon. In one embodiment, the delivery sheath is a polymer. The polymer may be, for example, poly(ethylene-vinyl acetate) (PEVA), polyurethane, polycaprolactone, phosphoryl choline, a blended polymer of polyurethane and polycaprolactone or any other polymer well known to those with skill in the art.

This method of manufacturing includes: providing an elongated catheter shaft having proximal and distal ends with an inflatable balloon located close to the distal end of the catheter shaft, wherein the balloon includes a polymeric material having a surface; positioning a (first) delivery sheath around the balloon, wherein the delivery sheath includes a polymeric material having a therapeutic agent impregnated therein or coated thereon; and applying conditions effective to transfer (e.g., diffuse) the therapeutic agent from the delivery sheath to the surface of the inflatable balloon.

In another embodiment of manufacturing a balloon cather as described herein, the method further includes: removing the delivery sheath from the balloon; positioning an elastomeric sheath around the balloon, wherein the elastomeric sheath includes an elastomeric material having a surface; positioning a (second) delivery sheath around the elastomeric sheath, wherein the delivery sheath includes a polymeric material having a therapeutic agent impregnated therein or coated thereon; and applying conditions effective to transfer (e.g., diffuse) the therapeutic agent from the delivery sheath to the surface of the elastomeric sheath.

In operation, the delivery sheath is wrapped or otherwise placed around the balloon or elastomeric sheath (advantageously the elastomeric sheath can be mounted on a mandrel assembly) so that the delivery sheath contacts the surface of the balloon or the surface of the elastomeric sheath. In this position, the therapeutic agent will be transferred (e.g., diffused) to the balloon or elastomeric sheath. The transfer of the therapeutic agent will continue until a state of equilibrium is reached or until the delivery sheath is removed from contact with the balloon or elastomeric sheath.

The application conditions effective to transfer the therapeutic agent from the delivery sheath to the surface of the balloon or elastomeric sheath include elevated temperatures and pressures (typically above room temperature). The higher these parameters, the faster the rate of transfer (e.g., diffusion). The maximum values would likely be those that damage the materials of the balloon, elastomeric sheath, and delivery sheath. For example, the temperature and pressure for transferring from a delivery sheath to a balloon made of Nylon-12 would be no greater than its melting temperature (190° C.-210° C. at ambient pressure), and preferably no greater than its heat distortion temperature, which is 150° C. at 0.45 MPa and 55° C. at 1.80 MPa.

Those of skill in the art will recognize that the method of loading the therapeutic agent disclosed herein using a delivery sheath allows for precise control of the amount loaded as well as allows for the loading of amounts below that allowed by current methods of application such as, for example, dipping, spraying, and brushing.

Methods of Use

In one embodiment of the present disclosure, there is provided a method of delivering one or more therapeutic agents to a diseased vessel.

Referring to FIG. 3, an exemplary general method includes: providing a balloon catheter 10 as described herein; advancing the balloon catheter 10 into the diseased vessel 30 (as shown in FIG. 3A); inflating the inflatable balloon to form an inflated balloon 15 and an expanded sheath 22 that contacts the wall of the diseased vessel 30 and thereby delivers the second therapeutic agent from the surface of the expanded sheath to a first site of the diseased vessel (as shown in FIG. 3B); deflating the inflated balloon to reform the inflatable balloon into a reformed inflatable balloon (not shown); removing the elastomeric sheath from around the reformed inflatable balloon (not shown); and inflating the reformed inflatable balloon (after removing the elastomeric sheath) to contact the wall of the diseased vessel 30 with the first therapeutic agent to deliver the first therapeutic agent from the surface of the inflated balloon 15 to the first site (as shown in FIG. 3C), or to a different site of the same or a different diseased vessel if the reformed inflatable balloon is moved to a different site after the expanded sheath contacts the wall of the diseased vessel and before inflating the reformed inflatable balloon.

Referring to FIG. 3A, a preferred method includes: providing a balloon catheter 10 that includes: an elongated catheter shaft 12 having a proximal end 14 and a distal end 16; a folded inflatable balloon 15 located close to the distal end 16 of the catheter shaft 12, wherein the balloon includes a polymeric material having a surface with a first therapeutic agent disposed thereon (as a result of the therapeutic agent being coated on the surface or impregnated into the polymeric material); and an elastomeric sheath 22 positioned around the folded inflatable balloon such that the inflatable balloon is located within the elastomeric sheath, wherein the sheath includes an elastomeric material having a surface with a second therapeutic agent disposed thereon (as a result of the therapeutic agent being coated on the surface or impregnated into the elastomeric material). The method further includes: advancing the balloon catheter 10 into the diseased vessel 30 (i.e., one having a vascular lesion); and (referring to FIG. 3B) inflating the inflatable balloon to form an inflated balloon 15 and an expanded sheath 22 that contacts the wall of the diseased vessel 30 and thereby delivers the second therapeutic agent from the surface of the expanded sheath to a first site of the diseased vessel. The method then includes deflating the inflated balloon after delivering the second therapeutic agent to the first site to reform the inflatable balloon into a reformed inflatable balloon (herein, a "reformed" inflatable balloon may or may not be refolded, and may or may not be the same degree of "deflation" of the initial inflatable balloon) (not shown); removing the elastomeric sheath 22 from around the reformed inflatable balloon (e.g., to a position shown in FIG. 3C); and (as shown in FIG. 3C) inflating the reformed inflatable balloon (after removing the elastomeric sheath) from the reformed inflatable balloon to contact the wall of the diseased vessel with the first therapeutic agent to deliver the first therapeutic agent from the surface of the inflated reformed inflatable balloon to the first site, or to a different site of the same or a different diseased vessel if the reformed inflatable balloon is moved to the different site after the expanded sheath contacts the wall of the diseased vessel and before inflating the reformed inflatable balloon. Folding, and thus also refolding, may be not necessary in case spherical balloons are used. These are typically quite small balloons (e.g., having outside diameter of about 1 mm).

In certain preferred methods, the balloon catheter further includes a protective sheath positioned around the elastomeric sheath and the inflatable balloon located in the elastomeric sheath, and the method further includes (as shown in FIG. 3A) removing the protective sheath 26 from the elastomeric sheath 22 after advancing the balloon catheter 10 into the diseased vessel 30.

In certain preferred methods, removing the elastomeric sheath from around the reformed inflatable balloon includes retracting the elastomeric sheath 22 towards the proximal end 14 of the catheter shaft 12 (as shown in FIG. 3A). This allows the balloon to stay at the same site of initial treatment or be advanced to a second, more distal site. Alternatively, removing the elastomeric sheath from around the reformed inflatable balloon includes advancing the reformed inflatable balloon to a second site of the diseased vessel that is distal from the first site.

In certain preferred methods, particularly those in which the therapeutic agent-coated portion of the elastomeric sheath is longer than the inflatable balloon, after inflating the inflatable balloon to form the inflated balloon and the expanded sheath and prior to removing the elastomeric sheath from around the reformed inflatable balloon, the method includes: retracting the inflatable balloon proximally towards the proximal end of the catheter shaft within the elastomeric sheath; inflating the inflatable balloon after retracting the inflatable balloon proximally so that the elastomeric sheath contacts the wall of the diseased vessel and thereby delivers the second therapeutic agent to a second site that is located proximally from the first site of the diseased vessel; and deflating the inflated balloon after delivering the second therapeutic agent at the second site (to again reform an inflatable balloon, wherein a "reformed" inflatable balloon may or may not be refolded, and may or may not be the same degree of "deflation" of the initial inflatable balloon or the "first reformed" inflatable balloon).

Referring to FIG. 4, in one embodiment of the present disclosure, there is provided an alternative method of delivering one or more therapeutic agents to a diseased vessel. The method includes: (referring to FIG. 4A) providing a balloon catheter 10 that includes: an elongated catheter shaft 12 having a proximal end 14 and a distal end 16; an inflatable balloon 15 (preferably, a folded inflatable balloon) located close to the distal end 16 of the catheter shaft 12 (i.e., closer to the distal end 16 of the catheter shaft 12 than the proximal end 14 of the catheter shaft 12), wherein the balloon has a proximal end 14' and a distal end 16', and wherein the balloon comprises a polymeric material having a surface with a first therapeutic agent disposed thereon (as a result of the therapeutic agent being coated on the surface or impregnated into the polymeric material); an elastomeric sheath 22 positioned around the inflatable balloon 15 such that the inflatable balloon is located within the elastomeric sheath, wherein the sheath comprises an elastomeric material having a surface with a second therapeutic agent disposed thereon (as a result of the therapeutic agent being coated on the surface or impregnated into the elastomeric material), and wherein the therapeutic agent-coated portion of the elastomeric sheath (hatched portion of sheath 22) is longer than the inflatable balloon; and a protective sheath 26 positioned around the elastomeric sheath 22 and the inflatable balloon 15.

Figure 4A:
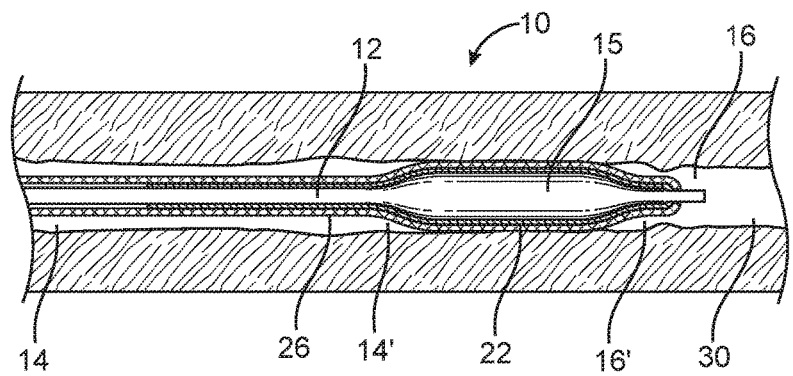
Figure 4B:
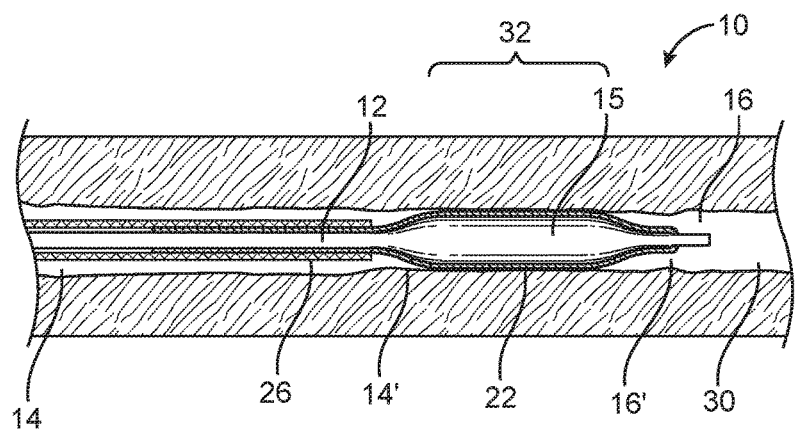

In a first delivery step, the method further includes: advancing the balloon catheter 10 into the diseased vessel 30 (to a lesion to be treated); and (as shown in FIG. 4B) retracting the protective sheath 26 towards the proximal end 14 of the catheter shaft 12 so that the inflatable balloon 15 is not located in the protective sheath 26; inflating the inflatable balloon to form an inflated balloon and an expanded sheath that contacts the wall of the diseased vessel and thereby delivers the second therapeutic agent from the surface of the expanded sheath to a first site 32 of the diseased vessel 30. The inflated balloon is then deflated after delivering the second therapeutic agent to the first site to reform the inflatable balloon into a reformed inflatable balloon (herein, this "first reformed" inflatable balloon may or may not be refolded, and may or may not be the same degree of "deflation" of the initial inflatable balloon).

Figure 4C:
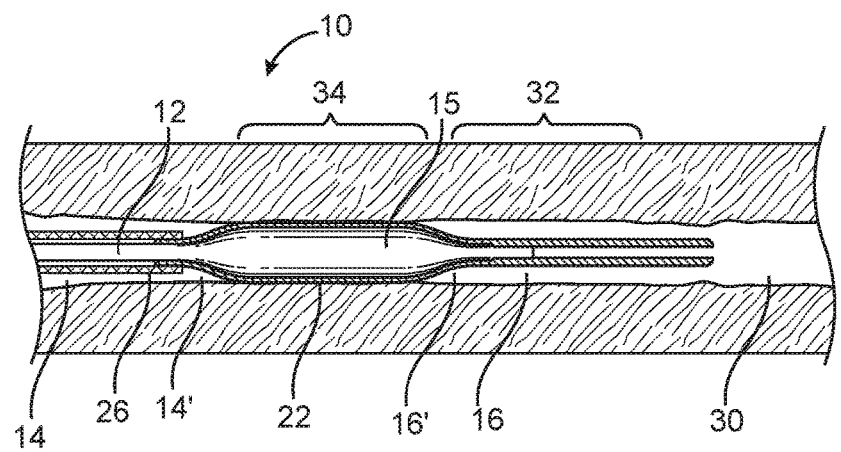

In a second delivery step, as shown in FIG. 4C, the method then includes retracting the protective sheath 26 proximally towards the proximal end 14 of the catheter shaft 12 so that the reformed inflatable balloon is not located in the protective sheath 26 after delivering the second therapeutic agent to the first site 32; retracting the reformed inflatable balloon 15 proximally towards the proximal end 14 of the catheter shaft 12 within the elastomeric sheath 22 after delivering the second therapeutic agent to the first site 32; and inflating the reformed inflatable balloon after retracting the reformed inflatable balloon and the protective sheath proximally so that the elastomeric sheath contacts the wall of the diseased vessel and thereby delivers the second therapeutic agent to a second site 34 that is located proximally from the first site of the diseased vessel. In FIG. 4C the second site 34 is shown adjacent to the first site 32. The (reformed) inflated balloon is deflated once again to reform the inflatable balloon (into a reformed inflatable balloon) after delivering the second therapeutic agent to the second site (herein, a "second reformed" inflatable balloon may or may not be refolded, and may or may not be the same degree of "deflation" of the initial inflatable balloon or the "first reformed" inflatable balloon).

Figure 4D:
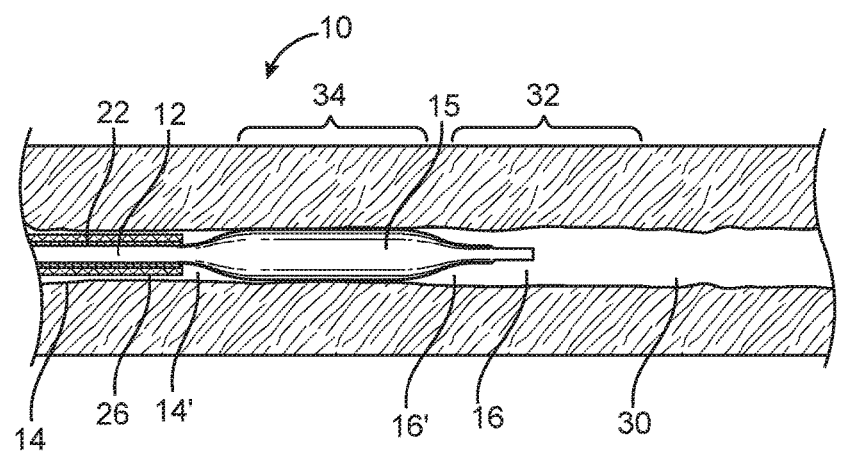

In a third delivery step, as shown in FIG. 4D, the method then includes retracting the elastomeric sheath 22 proximally towards the proximal end 14 of the catheter shaft 12 so that the reformed inflatable balloon 15 is not located in the protective sheath or the elastomeric sheath after delivering the second therapeutic agent to the second site 34; and inflating the reformed inflatable balloon 15 after retracting the elastomeric sheath 22 proximally to form an inflated balloon that contacts the wall of the diseased vessel and thereby delivers the first therapeutic agent from the surface of the inflated balloon to the second site 34 of the diseased vessel, or to a third site of the diseased vessel if the inflated balloon is moved to a different site after delivering the second therapeutic agent to the second site.

Using this method, a therapeutic agent may be delivered multiple times to various sites from the elastomeric sheath, although typically only once from the balloon.

In certain embodiments, the present disclosure may be particularly advantageous in case long or very long lesions are to be treated. In fact, because the therapeutic agent may be present both on the balloon and on at least a portion of the elastomeric sheath, only one catheter device may need to be used for treating lesions having a length equal to or lower than the sum of the coated balloon length and the coated elastomeric sheath length. In other words, because of the present disclosure it is not necessary to use two, or more than two, therapeutic agent-coated balloon catheters for treating a long or very long lesion, but only a single balloon catheter may be sufficient for achieving the same result. This clearly means saving of intervention time (since only one device has to be introduced into the blood vessel, tracked to the lesion and operated by the physician) as well as saving of money (since only one device may need to be used).

Moreover, even in the case the lesion to be treated is not remarkably long, the present disclosure may represent an advantageous solution with respect to the known devices since the balloon length may be selected to be sensibly lower than the lesion length due to the therapeutic agent-coated elastomeric sheath length, and thus may be used to treat the lesion in combination with the therapeutic agent coated balloon. This aspect is particularly favorable because manufacturing and coating a short balloon is easier and less expensive than manufacturing and coating a long or very long (up to 300 mm in length) balloon.

Exemplary Embodiments

Embodiment 1 is a balloon catheter comprising: an elongated catheter shaft having proximal and distal ends, wherein the catheter shaft defines a longitudinal axis extending between the proximal and distal ends; an inflatable balloon located closer to the distal end of the catheter shaft than the proximal end of the catheter shaft, wherein the balloon comprises a polymeric material having a surface with a first therapeutic agent disposed thereon (as a result of the therapeutic agent being coated on the surface or impregnated into the polymeric material); and an elastomeric sheath comprising an elastomeric material having a surface with a second therapeutic agent disposed thereon (as a result of the therapeutic agent being coated on the surface or impregnated into the elastomeric material); wherein in a first configuration the inflatable balloon is located within the elastomeric sheath such that expansion of the inflatable balloon to an inflated state expands the elastomeric sheath, and wherein in a second configuration the balloon is located outside of the elastomeric sheath, and further wherein the balloon and the sheath are configured for movement relative to each other along the longitudinal axis between the first configuration and the second configuration when deployed within a body lumen.

Embodiment 2 is the balloon catheter of embodiment 1 wherein the inflatable balloon is in a folded state when in the first configuration.

Embodiment 3 is the balloon catheter of embodiments 1 or 2 wherein the first and second therapeutic agents are different therapeutic agents.

Embodiment 4 is the balloon catheter of embodiments 1 or 2 wherein the first and second therapeutic agents are the same therapeutic agent.

Embodiment 5 is the balloon catheter of any of embodiments 1 through 4 wherein the first and second therapeutic agents are at different concentrations.

Embodiment 6 is the balloon catheter of any of embodiments 1 through 4 wherein the first and second therapeutic agents are at the same concentrations.

Embodiment 7 is the balloon catheter of any of embodiments 1 through 6 wherein the elastomeric material of the elastomeric sheath comprises polytetrafluoroethylene.

Embodiment 8 is the balloon catheter of any of embodiments 1 through 7 wherein the polymeric material of the balloon comprises a nylon or a polyethylene terephthalate.

Embodiment 9 is the balloon catheter of embodiments 1 through 8 further comprising an optional protective sheath positioned around the elastomeric sheath, wherein the protective sheath is configured for movement relative to the elastomeric sheath along the longitudinal axis, when deployed in a body lumen, between a first configuration in which the elastomeric sheath is positioned within the protective sheath and a second configuration in which at least a portion of the elastomeric sheath is located outside of the protective sheath.

Embodiment 10 is a method of manufacturing the balloon catheter of any of embodiments 1 through 9, the method comprising:
providing an elongated catheter shaft having proximal and distal ends with an inflatable balloon located closer to the distal end of the catheter shaft than the proximal end of the catheter shaft, wherein the balloon comprises a polymeric material having a surface;
positioning a delivery sheath around the balloon, wherein the delivery sheath comprises a polymeric material having a therapeutic agent impregnated therein or coated thereon; and
applying conditions effective to transfer (e.g., diffuse) the therapeutic agent from the delivery sheath to the surface of the inflatable balloon.

Embodiment 11 is the method of embodiment 10 further comprising: removing the delivery sheath from the balloon; positioning an elastomeric sheath around the balloon, wherein the elastomeric sheath comprises an elastomeric material having a surface; positioning a delivery sheath around the elastomeric sheath, wherein the delivery sheath comprises a polymeric material having a therapeutic agent impregnated therein or coated thereon; and applying conditions effective to transfer (e.g., diffuse) the therapeutic agent from the delivery sheath to the surface of the elastomeric sheath.

Embodiment 12 is a method of delivering one or more therapeutic agents to a diseased vessel, the method comprising: providing a balloon catheter of any of embodiments 1 through 9; advancing the balloon catheter into the diseased vessel; inflating the inflatable balloon to form an inflated balloon and an expanded sheath that contacts the wall of the diseased vessel and thereby delivers the second therapeutic agent from the surface of the expanded sheath to a first site of the diseased vessel; deflating the inflated balloon to reform the inflatable balloon into a reformed inflatable balloon ("reformed" inflatable balloon may or may not be refolded, and may or may not be the same degree of "deflation" of the initial inflatable balloon); removing the elastomeric sheath from around the reformed inflatable balloon; and inflating the reformed inflatable balloon to contact the wall of the diseased vessel with the first therapeutic agent to deliver the first therapeutic agent from the surface of the inflated balloon to the first site, or to a different site of the same or a different diseased vessel if the reformed inflatable balloon is moved to the different site after the expanded sheath contacts the wall of the diseased vessel and before inflating the reformed inflatable balloon.

Embodiment 13 is a method of delivering one or more therapeutic agents to a diseased vessel, the method comprising:
providing a balloon catheter comprising:
an elongated catheter shaft having proximal and distal ends;
a folded inflatable balloon located closer to the distal end of the catheter shaft than the proximal end of the catheter shaft, wherein the balloon comprises a polymeric material having a surface with a first therapeutic agent disposed thereon (as a result of the therapeutic agent being coated on the surface or impregnated into the polymeric material); and
an elastomeric sheath positioned around the folded inflatable balloon such that the inflatable balloon is located within the elastomeric sheath, wherein the sheath comprises an elastomeric material having a surface with a second therapeutic agent disposed thereon (as a result of the therapeutic agent being coated on the surface or impregnated into the elastomeric material);
advancing the balloon catheter into the diseased vessel;
inflating the folded inflatable balloon to form an inflated balloon and an expanded sheath that contacts the wall of the diseased vessel and thereby delivers the second therapeutic agent from the surface of the expanded sheath to a first site of the diseased vessel;
deflating the inflated balloon after delivering the second therapeutic agent to the first site to reform the inflatable balloon into a reformed inflatable balloon ("reformed" inflatable balloon may or may not be refolded, and may or may not be the same degree of "deflation" of the initial inflatable balloon);
removing the elastomeric sheath from around the reformed inflatable balloon; and
inflating the reformed inflatable balloon to contact the wall of the diseased vessel with the first therapeutic agent to deliver the first therapeutic agent from the surface of the inflated reformed inflatable balloon to the first site, or to a different site of the same or a different diseased vessel if the reformed inflatable balloon is moved to the different site after the expanded sheath contacts the wall of the diseased vessel and before inflating the reformed inflatable balloon.

Embodiment 14 is the method of embodiment 13 wherein the balloon catheter further comprises a protective sheath positioned around the elastomeric sheath and the inflatable balloon located in the elastomeric sheath, and the method further comprises removing the protective sheath from the elastomeric sheath after advancing the balloon catheter into the diseased vessel.

Embodiment 15 is the method of embodiment 13 or 14 wherein the diseased vessel comprises a vascular lesion having a length that is longer than the length of the balloon.

Embodiment 16 is the method of any of embodiments 12 through 15 wherein removing the elastomeric sheath from around the reformed inflatable balloon comprises retracting the sheath towards the proximal end of the catheter shaft (so the balloon can stay at the same site of initial treatment or be advanced to a second, more distal site).

Embodiment 17 is the method of any of embodiments 12 through 16 wherein removing the elastomeric sheath from around the reformed inflatable balloon comprises advancing the reformed inflatable balloon to a second site of the diseased vessel that is distal from the first site.

Embodiment 18 is the method of any of embodiments 12 through 17 wherein the elastomeric sheath is longer than the inflatable balloon; and wherein after inflating the inflatable balloon to form the inflated balloon and the expanded sheath and prior to removing the elastomeric sheath from around the reformed inflatable balloon, the method comprises: retracting the inflatable balloon proximally towards the proximal end of the catheter shaft within the elastomeric sheath; inflating the inflatable balloon after retracting the inflatable balloon proximally so that the elastomeric sheath contacts the wall of the diseased vessel and thereby delivers the second therapeutic agent to a second site that is located proximally from the first site of the diseased vessel; and deflating the inflated balloon after delivering the second therapeutic agent at the second site.

Embodiment 19 is a method of delivering one or more therapeutic agents to a diseased vessel, the method comprising:
providing a balloon catheter comprising:
an elongated catheter shaft having proximal and distal ends;
an inflatable balloon located closer to the distal end of the catheter shaft than the proximal end of the catheter shaft, wherein the balloon has a proximal end and a distal end, and wherein the balloon comprises a polymeric material having a surface with a first therapeutic agent disposed thereon (as a result of the therapeutic agent being coated on the surface or impregnated into the polymeric material);
an elastomeric sheath positioned around the inflatable balloon such that the inflatable balloon is located within the elastomeric sheath, wherein the sheath comprises an elastomeric material having a surface with a second therapeutic agent disposed thereon (as a result of the therapeutic agent being coated on the surface or impregnated into the elastomeric material), and wherein the elastomeric sheath is longer than the inflatable balloon; and
a protective sheath positioned around the elastomeric sheath and the inflatable balloon;
advancing the balloon catheter into the diseased vessel;
retracting the protective sheath towards the proximal end of the catheter shaft so that the inflatable balloon is not located in the protective sheath;
inflating the inflatable balloon to form an inflated balloon and an expanded sheath that contacts the wall of the diseased vessel and thereby delivers the second therapeutic agent from the surface of the expanded sheath to a first site of the diseased vessel;
deflating the inflated balloon after delivering the second therapeutic agent to the first site to reform the inflatable balloon into a reformed inflatable balloon (this "first reformed" inflatable balloon may or may not be refolded, and may or may not be the same degree of "deflation" of the initial inflatable balloon);
retracting the protective sheath proximally towards the proximal end of the catheter shaft so that the reformed inflatable balloon is not located in the protective sheath after delivering the second therapeutic agent to the first site;
retracting the reformed inflatable balloon proximally towards the proximal end of the catheter shaft within the elastomeric sheath (after delivering the second therapeutic agent to the first site);
inflating the reformed inflatable balloon (after retracting the inflatable balloon and the protective sheath proximally) so that the elastomeric sheath contacts the wall of the diseased vessel and thereby delivers the second therapeutic agent to a second site that is located proximally from the first site of the diseased vessel;
deflating the reformed inflated balloon to again reform a reformed inflatable balloon after delivering the second therapeutic agent to the second site (to form a second reformed inflatable balloon, wherein this "second reformed" inflatable balloon may or may not be refolded, and may or may not be the same degree of "deflation" of the initial or "first reformed" inflatable balloon);
retracting the elastomeric sheath proximally towards the proximal end of the catheter shaft so that the reformed inflatable balloon is not located in the protective sheath or the elastomeric sheath after delivering the second therapeutic agent to the second site; and
inflating the reformed inflatable balloon (after retracting the elastomeric sheath proximally) to form an inflated balloon that contacts the wall of the diseased vessel and thereby delivers the first therapeutic agent from the surface of the inflated balloon to the second site of the diseased vessel, or to a third site of the diseased vessel if the inflated balloon is moved to the different site after delivering the second therapeutic agent to the second site.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed:
1. A method of delivering one or more therapeutic agents to a diseased vessel, the method comprising:
providing a balloon catheter comprising:
an elongated catheter shaft having proximal and distal ends;
a folded inflatable balloon located close to the distal end of the catheter shaft, wherein the balloon comprises a polymeric material having a surface with a first therapeutic agent disposed thereon; and
an elastomeric sheath positioned around the folded inflatable balloon such that the inflatable balloon is located within the elastomeric sheath, wherein the sheath comprises an elastomeric material having a surface with a second therapeutic agent disposed thereon;
advancing the balloon catheter into the diseased vessel;
inflating the folded inflatable balloon to form an inflated balloon and an expanded sheath that contacts the wall of the diseased vessel and thereby delivers the second therapeutic agent from the surface of the expanded sheath to a first site of the diseased vessel;
deflating the inflated balloon after delivering the second therapeutic agent to the first site to reform the inflatable balloon into a reformed inflatable balloon;

removing the elastomeric sheath from around the reformed inflatable balloon; and inflating the reformed inflatable balloon to contact the wall of the diseased vessel with the first therapeutic agent to deliver the first therapeutic agent from the surface of the inflated reformed inflatable balloon to the first site, or to a different site of the same or a different diseased vessel if the reformed inflatable balloon is moved to the different site after the expanded sheath contacts the wall of the diseased vessel and before inflating the reformed inflatable balloon.

2. The method of claim 1 wherein the balloon catheter further comprises a protective sheath positioned around the elastomeric sheath and the inflatable balloon located in the elastomeric sheath, and the method further comprises removing the protective sheath from the elastomeric sheath after advancing the balloon catheter into the diseased vessel.

3. The method of claim 1 wherein the diseased vessel comprises a vascular lesion having a length that is longer than the length of the balloon.

4. The method of claim 1 wherein removing the elastomeric sheath from around the reformed inflatable balloon comprises retracting the sheath towards the proximal end of the catheter shaft.

5. The method of claim 1 wherein the elastomeric sheath is longer than the inflatable balloon; and wherein after inflating the inflatable balloon to form the inflated balloon and the expanded sheath and prior to removing the elastomeric sheath from around the reformed inflatable balloon, the method comprises:

retracting the inflatable balloon proximally towards the proximal end of the catheter shaft within the elastomeric sheath;

inflating the inflatable balloon after retracting the inflatable balloon proximally so that the elastomeric sheath contacts the wall of the diseased vessel and thereby delivers the second therapeutic agent to a second site that is located proximally from the first site of the diseased vessel; and deflating the inflated balloon after delivering the second therapeutic agent at the second site.

6. A method of delivering one or more therapeutic agents to a diseased vessel, the method comprising:

providing a balloon catheter comprising:

an elongated catheter shaft having proximal and distal ends;

a folded inflatable balloon located close to the distal end of the catheter shaft, wherein the balloon comprises a polymeric material having a surface with a first therapeutic agent disposed thereon; and an elastomeric sheath positioned around the folded inflatable balloon such that the inflatable balloon is located within the elastomeric sheath, wherein the sheath comprises an elastomeric material having a surface with a second therapeutic agent disposed thereon;

advancing the balloon catheter into the diseased vessel;

inflating the folded inflatable balloon to form an inflated balloon and an expanded sheath that contacts the wall of the diseased vessel and thereby delivers the second therapeutic agent from the surface of the expanded sheath to a first site of the diseased vessel;

deflating the inflated balloon after delivering the second therapeutic agent to the first site to reform the inflatable balloon into a reformed inflatable balloon;

removing the elastomeric sheath from around the reformed inflatable balloon, wherein removing the elastomeric sheath from around the reformed inflatable balloon comprises advancing the reformed inflatable balloon to a second site of the diseased vessel that is distal from the first site; and inflating the reformed inflatable balloon to contact the wall of the diseased vessel with the first therapeutic agent to deliver the first therapeutic agent from the surface of the inflated reformed inflatable balloon to the first site, or to a different site of the same or a different diseased vessel if the reformed inflatable balloon is moved to the different site after the expanded sheath contacts the wall of the diseased vessel and before inflating the reformed inflatable balloon.

7. The method of claim 6 wherein the balloon catheter further comprises a protective sheath positioned around the elastomeric sheath and the inflatable balloon located in the elastomeric sheath, and the method further comprises removing the protective sheath from the elastomeric sheath after advancing the balloon catheter into the diseased vessel.

8. The method of claim 6 wherein the diseased vessel comprises a vascular lesion having a length that is longer than the length of the balloon.

9. A method of delivering one or more therapeutic agents to a diseased vessel, the method comprising:

providing a balloon catheter comprising:

an elongated catheter shaft having proximal and distal ends;

an inflatable balloon located close to the distal end of the catheter shaft, wherein the balloon has a proximal end and a distal end, and wherein the balloon comprises a polymeric material having a surface with a first therapeutic agent disposed thereon;

an elastomeric sheath positioned around the inflatable balloon such that the inflatable balloon is located within the elastomeric sheath, wherein the sheath comprises an elastomeric material having a surface with a second therapeutic agent disposed thereon, and wherein the elastomeric sheath is longer than the inflatable balloon; and a protective sheath positioned around the elastomeric sheath and the inflatable balloon;

advancing the balloon catheter into the diseased vessel;

retracting the protective sheath towards the proximal end of the catheter shaft so that the inflatable balloon is not located in the protective sheath;

inflating the inflatable balloon to form an inflated balloon and an expanded sheath that contacts the wall of the diseased vessel and thereby delivers the second therapeutic agent from the surface of the expanded sheath to a first site of the diseased vessel;

deflating the inflated balloon after delivering the second therapeutic agent to the first site to reform the inflatable balloon into a reformed inflatable balloon;

retracting the protective sheath proximally towards the proximal end of the catheter shaft so that the reformed inflatable balloon is not located in the protective sheath after delivering the second therapeutic agent to the first site;

retracting the reformed inflatable balloon proximally towards the proximal end of the catheter shaft within the elastomeric sheath;

inflating the reformed inflatable balloon so that the elastomeric sheath contacts the wall of the diseased vessel and thereby delivers the second therapeutic agent to a second site that is located proximally from the first site of the diseased vessel;

deflating the reformed inflated balloon to again reform a reformed inflatable balloon after delivering the second therapeutic agent to the second site;

retracting the elastomeric sheath proximally towards the proximal end of the catheter shaft so that the reformed inflatable balloon is not located in the protective sheath or the elastomeric sheath after delivering the second therapeutic agent to the second site; and inflating the reformed inflatable balloon to form an inflated balloon that contacts the wall of the diseased vessel and thereby delivers the first therapeutic agent from the surface of the inflated balloon to the second site of the diseased vessel, or to a third site of the diseased vessel if the inflated balloon is moved to the different site after delivering the second therapeutic agent to the second site.

\* \* \* \* \*